United States Patent [19]
Mark et al.

[11] 4,182,838
[45] Jan. 8, 1980

[54] POLYCARBONATE COMPOSITIONS HAVING IMPROVED FLAME RETARDANCE AND IMPROVED WATER VAPOR TRANSMISSION

[75] Inventors: Victor Mark, Evansville; Charles V. Hedges, Mt. Vernon, both of Ind.

[73] Assignee: General Electric Company, Pittsfield, Mass.

[21] Appl. No.: 882,126

[22] Filed: Feb. 28, 1978

[51] Int. Cl.$^2$ ............................................. C08G 63/62
[52] U.S. Cl. ................................. 528/202; 252/182; 568/722; 528/205; 568/726
[58] Field of Search ............. 260/47 XA, 77.5 D, 463

[56] References Cited

U.S. PATENT DOCUMENTS

| | | | |
|---|---|---|---|
| 3,028,365 | 4/1962 | Schnell | 260/47 |
| 3,062,781 | 11/1962 | Buttenbruch | 260/47 |
| 3,991,120 | 11/1976 | Ladd | 260/613 B |

*Primary Examiner*—Theodore E. Pertilla
*Attorney, Agent, or Firm*—Salvatore C. Mitri; William F. Mufatti

[57] ABSTRACT

Improved flame retardance and improved water vapor transmission are imparted to high molecular weight aromatic polycarbonate resins by selecting appropriate diphenols and controlling the degree to which these particular diphenols are halogenated.

6 Claims, No Drawings

POLYCARBONATE COMPOSITIONS HAVING IMPROVED FLAME RETARDANCE AND IMPROVED WATER VAPOR TRANSMISSION

This invention relates to aromatic polycarbonate resins having improved flame retardance and improved water vapor transmission.

BACKGROUND OF THE INVENTION

Polycarbonate polymers are known as being excellent molding materials since products made therefrom exhibit such properties as high impact strength, toughness, high transparency, wide temperature limits (high impact resistance below −60° C. and a UL thermal endurance rating of 115° C. with impact), good dimensional stability, good creep resistance, and the like. It would be desirable to add to this list of properties that of improved flame retardance so that products made from such polycarbonate polymers could be safely used by the consumer and also meet the increasing requirements of certain flame retardant criteria being established by local and federal government agencies as well as the manufacturers of such products. It would also be desirable to improve the moisture barrier property of such polycarbonates thereby enabling them to be used in a wider range of product applications.

It is known to obtain polycarbonates which contain halogenated monomers as their main, polymeric building blocks. For example, U.S. Pat. No. 3,028,365 discloses a host of polycarbonate compositions including tetrabromobisphenol-A and a dichloromethylenediphenol monomer, as well as processes for obtaining these polycarbonates.

U.S. Pat. No. 3,062,781 discloses that halogenated polycarbonates can be obtained by first halogenating a diphenol containing at least two halogen substituents. However, the only dihalogenated diphenol disclosed is dichlorobisphenol-A.

German Pat. No. P25 20 317.2 discloses that halogenated polycarbonates can be obtained by halogenating bisphenol-A (4,4′-isopropylidenediphenol) to produce a mixture of unreacted bisphenol-A and statistical mixtures of halogenated bisphenol-A (BPA). The halogenated bisphenols disclosed comprise, primarily, tri- and tetrahalogenated BPA.

In general, these prior art references recognize that flame retardance can be imparted to polycarbonates by halogenating the monomeric building blocks from which they are obtained. In addition, these references suggest that the greater the degree of halogenation of the monomer, the better will be the fire retardance imparted to the polymer. U.S. Pat. No. 3,062,781 also indicates that halogenated diphenols have reduced permeability to steam. However, none of these references discloses or suggests that a high molecular weight aromatic polycarbonate resin having improved flame retardance as well as improved water vapor transmission can be obtained from particular halogenated diphenols.

SUMMARY OF THE INVENTION

It has now been found that improved flame retardance and water vapor transmission can be imparted to high molecular weight, aromatic polycarbonate resins by selecting appropriate diphenols to be halogenated. In general, this is accomplished by controlling the degree to which the particular diphenols are halogenated. Accordingly, the diphenols are halogenated so that there are obtained either highly pure dihalogenated diphenols or predetermined statistical mixtures comprising predominantly mono- and dihalogenated diphenols together with some unreacted diphenol.

Preferably, these predetermined, statistical, halogenated diphenol mixtures can be continuously obtained by either: (1) dissolving or suspending the diphenol in a solvent system comprising methylene chloride and water and thereafter introducing a halogen into the solvent system; or, (2) dissolving or suspending the diphenol in methylene chloride and then reacting the diphenol with sulfuryl chloride and, optionally, introducing another halogen therein; or, (3) dissolving or suspending the diphenol in methylene chloride and then introducing a halogen therein while concurrently purging the reaction with an inert gas. These processes are described in co-pending applications Ser. No. 882,192, filed Feb. 28, 1978, Ser. No. 882,242, filed Feb. 28, 1978, and Ser. No. 882,191, filed Feb. 28, 1978, respectively, all of which are assigned to the same assignee of this case.

While any of the halogens can be employed, chlorine and bromine are preferred. Thus, the diphenols that can be used to obtain the high molecular weight aromatic polycarbonates of the invention can be represented by the general formula

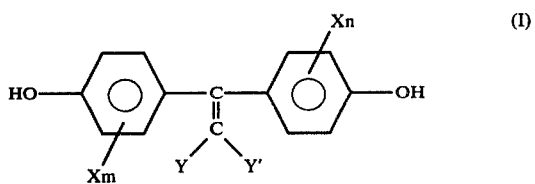

wherein Xm and Xn can each independently be a halogen and mixtures thereof; m and n are each 0.0 to about 2.5 with the proviso that m+n equal at least 0.1 and not more than about 2.5; and, Y and Y′ can independently be hydrogen and a halogen, preferably chlorine or bromine. In formula I above, the values for m and n represent the number of halogen substituents per mole of monomer.

It is possible to employ two or more different diphenols or a copolymer with a glycol or with hydroxy or acid terminated polyester, or with a dibasic acid in the event a carbonate copolymer or interpolymer rather than a homopolymer is desired for use in preparing the aromatic polycarbonate. Blends of any of these materials can also be used to obtain the aromatic polycarbonates.

These halogenated diphenols can then be employed to obtain the high molecular weight aromatic polycarbonates of the invention which can be linear or branched homopolymers or copolymers as well as mixtures thereof or polymeric blends and which generally have an intrinsic viscosity (IV) or about 0.40–1.0 dl/g as measured in methylene chloride at 25° C. These high molecular weight aromatic polycarbonates can be typically prepared by reacting the halogenated diphenol with a carbonate precursor.

The carbonate precursor used can be either a carbonyl halide, a carbonate ester or a haloformate. The carbonyl halides can be carbonyl bromide, carbonyl chloride and mixtures thereof. The carbonate esters can be diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonate such as di(tolyl) carbonate, etc., di-(naphthyl) carbonate, di-(chloronaphthyl) carbonate, phenyl tolyl carbonate, chlorophenyl chloronapthyl carbonate, etc., or mixtures thereof. The haloformates that can be used include bis-haloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid such as are disclosed in U.S. Pat. No. 3,169,121 which is incorporated herein by reference.

Molecular weight regulators, acid acceptors and catalysts can also be used in obtaining the aromatic polycarbonates of this invention. The useful molecular weight regulators include monohydric phenols such as phenol, chroman-I, paratertiarybutylphenol, parabromophenol, primary and secondary amines, etc. Preferably, phenol is employed as the molecular weight regulator.

A suitable acid acceptor can be either an organic or an inorganic acid acceptor. A suitable organic acid acceptor is a tertiary amine such as pyridine, triethylamine, dimethylaniline, tributylamine, etc. The inorganic acid acceptor can be either a hydroxide, a carbonate, a bicarbonate, or a phosphate of an alkali or alkaline earth metal.

The catalysts which can be employed are those that typically aid the polymerization of the diphenol with phosgene. Suitable catalysts include tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butyl ammonium iodide, benzyltrimethyl ammonium chloride and quaternary phosphonium compounds such as, for example, n-butyltriphenyl phosphonium bromide and methyl triphenyl phosphonium bromide.

Also included herein are branched polycarbonates wherein a polyfunctional aromatic compound is reacted with the diphenol and carbonate precursor to provide a thermoplastic randomly branched polycarbonate. These polyfunctional aromatic compounds contain at least three functional groups which are carboxyl, carboxylic anhydride, haloformyl, or mixtures thereof. Illustrative of polyfunctional aromatic compounds which can be employed include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride and trimellitic acid or their acid halide derivatives.

Blends of linear and branched aromatic polycarbonates are also included within the scope of this invention.

Other well known materials can also be employed for their intended function and include such materials as anti-static agents, mold release agents, thermal stabilizers, ultraviolet light stabilizers, reinforcing fillers such as glass and other inert fillers, foaming agents, and the like.

Accordingly, the high molecular weight aromatic polycarbonates of the invention can be represented by the general formula

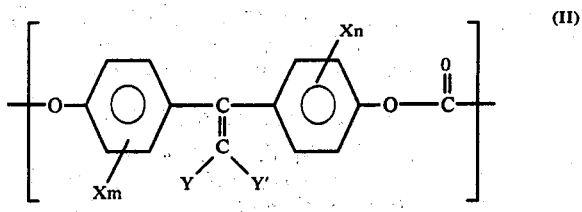

wherein Xm, Xn, m, n, Y and Y' are the same as identified in formula I above.

PREFERRED EMBODIMENT OF THE INVENTION

The following examples are set forth to more fully and clearly illustrate the present invention and are intended to be, and should be construed as being, exemplary and not limitative of the invention. Unless otherwise stated, all parts and percentages are by weight.

In the following examples, the flame retardancy of the polycarbonates obtained was determined by feeding the polycarbonates into an extruder which was operated at about 265° C. and the extrudates were each comminuted into pellets. The pellets were then injection molded at about 315° C. into test bars of about 5 in. by ½ in. by about 1/16-⅛ in. thick. The test bars (5 for each polycarbonate) were then subject to the test procedure set forth in Underwriter's Laboratories, Inc. Bulletin UL-94, Burning Test for Classifying Materials. In accordance with this test procedure, materials so investigated are rated either V-0, V-I, V-II based on the results of 5 specimens. The criteria for each V (for vertical) rating per UL-94 is briefly as follows:

"V-0": Average flaming and/or glowing after removal of the igniting flame shall not exceed 5 seconds and none of the specimens shall drip flaming particles which ignite absorbent cotton.

"V-I": Average flaming and/or glowing after removal of the igniting flame shall not exceed 25 seconds and the glowing does not travel vertically for more than ⅛" of the specimen after flaming ceases and glowing is incapable of igniting absorbent cotton.

"V-II": Average flame and/or glowing after removal of the igniting flame shall not exceed 25 seconds and the specimens drip flaming particles which ignite absorbent cotton.

In addition, a test bar which continues to burn for more than 25 seconds after removal of the igniting flame is classified, not by UL-94, but by the standards of the instant invention, as "burns". Further, UL-94 requires that all test bars in each test group must meet the V type rating to achieve the particular classification. Otherwise, the 5 bars receive the rating of the worst single bar. For example, if one bar is classified as V-II and the other four (4) are classified as V-0, then the rating for all would be V-II.

The moisture barrier properties for the polycarbonates and copolycarbonates in the ensuing examples were determined using Modern Controls, Inc. instruments, i.e., water vapor transmission rate (WVTR) measurements were obtained on an IRD-2C instrument pursuant to ASTM F-372-73. This method is based on infrared analysis and the results obtained are expressed in grams/24 hrs./100 in.$^2$/mil at 100° F. and 90% relative humidity (RH).

EXAMPLE 1

Preparation of a New Compound:
2,2'-Dichloro-4,4'-(dichlorovinylidene)diphenol (DCDVD)

Into a slurry of 281.14 parts by weight (1.0 partmole) of 4,4'-(dichlorovinylidene)diphenol (DVD) in 2000 parts by volume methylene chloride that was purged continuously with a slow stream of nitrogen, there was introduced, at ambient temperature, in the course of ca. 5 hours, 142 parts by weight (2.0 partmole) of chlorine gas. At the end of the slightly exothermic reaction, only a small amount of DVD remained undissolved. This was filtered off and the essentially colorless solution was analyzed by gas chromatography, which indicated the following composition:

| Compound | Retention Time (Min.) | Composition (Mole %) |
|---|---|---|
| 4,4'-(dichlorovinylidene)diphenol (DVD) | 18.97 | 0.2 |
| 2-chloro-4,4'-(dichlorovinylidene)diphenol (CDVD) | 20.11 | 8.6 |
| 2,2'-dichloro-4,4'-(dichlorovinylidene)diphenol (DCDVD) | 20.91 | 91.0 |
| 2,2',6'-trichloro-4,4'-(dichlorovinylidene)diphenol (TCDVD) | 21.91 | 0.2 |
| p-cumylphenol (reference) | 12.36 | |

Incremental addition of 2.8 parts by weight of more chlorine raised the assay of dichloro-DVD (DCDVD) as follows:

| Compound | Composition (Mole %) |
|---|---|
| DVD | 0 |
| CDVD | 2.2 |
| DCDVD | 93.7 |
| TCDVD | 4.1 |

Washings of the nearly colorless methylene chloride solution with water produced a yellow methylene chloride solution that was separated from the aqueous phase. Circa one-fourth of its volume of methanol was added to it and decolorized by stirring the yellow solution with 5 parts by weight zinc powder for about 1 hour. Filtration and evaporation of the solvent mixture on a rotary evaporator left behind a white crystalline mass that was recrystallized from a mixture of hexane and cyclohexane (1.0:1.5 volume ratio). The colorless crystals of 2,2'-dichloro-4,4'-(dichlorovinylidene)diphenol thus obtained had an assay of 99.1% and a melting point of 110.0°–110.5° C. Elemental analysis confirmed its composition. Chlorine: found, 40.6; theoretical, 40.5%. Carbon: found, 48.0; theoretical, 48.0%. Hydrogen: found, 2.2; theoretical, 2.3%.

EXAMPLE 2

Preparation of the polycarbonate of 2,2'-Dichloro-4,4'-(dichlorovinylidene)diphenol Into a mixture of 87.5 parts by weight (0.25 partmole) 2,2'-dichloro-4,4'-(dichlorovinylidene)diphenol (DCDVD), 300 parts by volume water, 300 parts by volume methylene chloride, 0.47 parts by weight phenol and 0.5 parts by weight triethylamine, there was introduced, at ambient temperature, 30 parts by weight phosgene in 30 minutes while maintaining the pH value of the two-phase system at approximately 11 (between 10 and 12.5) by simultaneously adding a 25 percent sodium hydroxide solution. At the end of the addition period, the pH of the aqueous phase was 11.4 and the DCDVD content of this phase was less than 1 part per million, as determined by ultraviolet analysis. The methylene chloride phase was separated from the aqueous phase, washed with an excess of dilute (0.01 normal) aqueous hydrochloric acid, and three times with deionized water. The polymer was precipitated by adding the neutral and salt-free methylene chloride solution to an excess of methanol and filtering off the white polymer, which was dried at 95° C. The resultant pure DCDVD polycarbonate had the properties shown in the Table.

EXAMPLE 3

The procedure of Example 2 was repeated except that DCDVD was replaced with a mixture of 43.75 parts by weight DCDVD (0.125 partmole) and 28.5 parts by weight 4,4'-isopropylidenediphenol, (BPA) (0.125 partmole). Work-up of the reaction product yielded a copolycarbonate with the properties shown in the Table.

EXAMPLE 4

The procedure of Example 2 was repeated, except that DCDVD was replaced with a mixture consisting of 21.9 parts by weight DCDVD (0.0625 partmole) and 42.75 parts by weight 4,4'-isopropylidenediphenol (BPA) (0.1875 partmole). The resultant polycarbonate had the properties shown in the Table.

EXAMPLE 5

Preparation of a New Ternary Composition

The procedure of Example 1 was repeated except that 71.0 parts by weight (1.0 partmole) chlorine was employed. At the end of the reaction, gas chromatographic analysis indicated the following composition:

| Diphenol Compound | Retention Time (Min.) | Composition (Mole %) |
|---|---|---|
| 4,4'-(dichlorovinylidene)phenol | 20.80 | 28.7 |
| 2-chloro-4,4'-(dichlorovinylidene)diphenol | 22.34 | 45.2 |
| 2,2'-dichloro-4,4'-(dichlorovinylidene)diphenol | 23.52 | 26.1 |
| p-cumylphenol (reference) | 15.32 | |

EXAMPLE 6

The procedure of Example 2 was repeated except for substituting an equivalent amount of the ternary mixture (78.9 parts by weight) obtained in Example 5, for the 87.5 parts by weight of DCDVD. A colorless, tough polycarbonate was obtained having the properties set forth in the Table.

EXAMPLE 7

Preparation of a New Compound:
2,2'-Dibromo-4,4'-(dichlorovinylidene)diphenol

The procedure of Example 1 was repeated, except that the chlorine gas was replaced with an equivalent amount of liquid bromine (320.0 parts by weight, 2 partmole), diluted with five fold its volume of methylene chloride. After decolorization with zinc powder and purification by charcoaling a white crystalline mass, comprising 2,2'-dibromo-4,4'-(dichlorovinylidene)diphenol was obtained that, after recrystallization from a hexane-cyclohexane mixture (1:1) yielded white crystals of 97.8% purity and 107.5°–108.5° C. melting point. Elemental analysis confirmed the composition. Chlorine: found 16.1; theoretical, 16.2% Bromine: found 36.6; theoretical, 36.4%. Carbon: found, 38.1; theoretical, 38.3%. Hydrogen: found, 1.8; theoretical, 1.8%.

EXAMPLE 8

The procedure of Example 2 was repeated except that 109.7 parts by weight (0.25 partmole) of 2,2'-dibromo-4,4'-(dichlorovinylidene)diphenol was used in place of DCDVD. A polycarbonate was obtained having the properties set forth in the Table.

TABLE

Properties of Polycarbonates and Copolycarbonates

| Example No. | I.V. | UL Rating Specimen Thickness | | WVTR |
|---|---|---|---|---|
| | | 1.56 mm | 3.13 mm | |
| 2 | 0.55 | V-O | V-O | 1.4 |
| 3 | 0.588 | V-O | V-O | 3.3 |
| 4 | 0.592 | V-O | V-O | 6.1 |
| 6 | 0.576 | V-O | V-O | 1.8 |
| 8 | 0.482 | V-O | V-O | 3.0 |

As the results in the foregoing table reveal, excellent flame retardance is imparted to the polycarbonates and copolycarbonates of the invention while concurrently improving their water vapor transmission properties.

What is claimed is:

1. A high molecular weight aromatic polycarbonate having improved flame retardance and improved water vapor transmission, said polycarbonate having an I.V. of about 0.40–1.0 dl/g. and being represented by the general formula

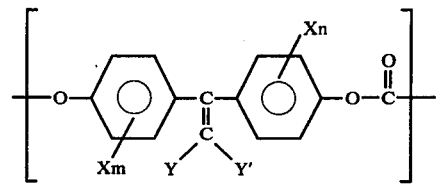

wherein $X_m$ and $X_n$ can each independently be a halogen and mixtures thereof; m and n are each 0.0 to about 2.5 with the proviso that m+n equal at least 0.1, but no more than about 2.5 and, Y and Y' can independently be hydrogen and a halogen.

2. The polycarbonate of claim 1 wherein $X_m$ and $X_n$ are each chlorine.

3. The polycarbonate of claim 1 wherein $X_m$ and $X_n$ are each bromine.

4. The polycarbonate of claim 1 wherein m+n equal 1.5.

5. The polycarbonate of claim 1 wherein Y and Y' are each hydrogen.

6. The polycarbonate of claim 1 wherein Y and Y' are each chlorine or bromine.

* * * * *